US010772605B2

(12) United States Patent
Morimoto (10) Patent No.: US 10,772,605 B2
(45) Date of Patent: *Sep. 15, 2020

(54) ULTRASONIC ENDOSCOPE AND METHOD OF MANUFACTURING THE SAME

(71) Applicant: FUJIFILM Corporation, Tokyo (JP)

(72) Inventor: Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 894 days.

This patent is subject to a terminal disclaimer.

(21) Appl. No.: 15/341,527

(22) Filed: Nov. 2, 2016

(65) Prior Publication Data

US 2017/0128043 A1 May 11, 2017

(30) Foreign Application Priority Data

Nov. 9, 2015 (JP) .................................. 2015-219041

(51) Int. Cl.
*A61B 8/00* (2006.01)
*A61B 1/00* (2006.01)
(Continued)

(52) U.S. Cl.
CPC ............ *A61B 8/445* (2013.01); *A61B 1/0011* (2013.01); *A61B 8/12* (2013.01); *A61B 8/4494* (2013.01); *A61B 8/56* (2013.01); *G10K 11/30* (2013.01)

(58) Field of Classification Search
CPC .............. A61B 1/0011; A61B 1/00112; A61B 1/00114; A61B 1/00121; A61B 1/00064;
(Continued)

(56) References Cited

U.S. PATENT DOCUMENTS 4,404,315 A * 9/1983 Tsukagoshi .............. C08K 3/04
524/495
6,149,598 A 11/2000 Tanaka
(Continued)

FOREIGN PATENT DOCUMENTS

CN 104644212 A 5/2015
JP 5-18509 U 3/1993
(Continued)

OTHER PUBLICATIONS

European Office Action, dated Mar. 20, 2018, for European Application No. 16197688.1.
(Continued)

*Primary Examiner* — Carolyn A Pehlke
(74) *Attorney, Agent, or Firm* — Birch, Stewart, Kolasch & Birch, LLP (57) ABSTRACT

The present invention provides an ultrasonic endoscope in which wiring can be reliably fixed to a wire housing space of an ultrasonic-oscillator housing part, and a method of manufacturing the ultrasonic endoscope. According to the present invention, a wire housing space is encapsulated from the outside by sealing a gap formed between an ultrasonic oscillator and an ultrasonic-oscillator housing part with sealing members. With this configuration, the wire housing space can be sufficiently filled with filling agent for fixing wires in the wire housing space. This achieves an ultrasonic endoscope in which the wires can be reliably fixed to the wire housing space of the ultrasonic-oscillator housing part.

18 Claims, 11 Drawing Sheets

(51) Int. Cl.
*A61B 8/12* (2006.01)
*G10K 11/30* (2006.01)

(58) Field of Classification Search
CPC ..... A61B 1/0008; A61B 8/445; A61B 8/4444; A61B 8/4455; A61B 8/4494; A61B 8/12; G10K 11/30
See application file for complete search history.

(56) References Cited

U.S. PATENT DOCUMENTS

| | | |
|---|---|---|
| 2002/0122246 A1 | 9/2002 | Tearney et al. |
| 2007/0167814 A1 | 7/2007 | Wakabayashi et al. |
| 2007/0266792 A1 | 11/2007 | Oosawa |
| 2009/0234233 A1 | 9/2009 | Nagano et al. |
| 2009/0253955 A1 | 10/2009 | Akiba |
| 2014/0058269 A1* | 2/2014 | Irie .................. A61B 8/4444 600/462 |
| 2015/0141825 A1 | 5/2015 | Kiyose |
| 2016/0183914 A1 | 6/2016 | Fujimura |

FOREIGN PATENT DOCUMENTS

| | | |
|---|---|---|
| JP | 6-335481 A | 12/1994 |
| JP | 9-75345 A | 3/1997 |
| JP | 2002-113005 A | 4/2002 |
| JP | 2007-68563 A | 3/2007 |
| JP | 2013-27695 A | 2/2013 |
| WO | WO 2015/053044 A1 | 4/2015 |

OTHER PUBLICATIONS

Japanese Office Action dated Dec. 14, 2018, for corresponding Japanese Application No. 2015-220042, with an English translation.
Extended European Search Report, dated Jun. 26, 2017, for European Application No. 16197600.6.
Partial European Search Report, dated Mar. 13, 2017, for corresponding European Application No. 16197600.6.
Extended European Search Report dated Mar. 2, 2017, for European Application No. 16197688.1.
Japanese Office Action for Japanese Application No. 2015-220042, dated Jul. 8, 2019, with English translation.
Chinese Office Action and Search Report dated Jun. 9, 2020, for Chinese Patent Application No. 201610982411.4, with an English translation.
Chinese Office Action and Search Report dated May 25, 2020, for Chinese Patent Application No. 201610982128.1, with an English translation.

* cited by examiner

ULTRASONIC ENDOSCOPE AND METHOD OF MANUFACTURING THE SAME

CROSS-REFERENCE TO RELATED APPLICATIONS

The present application claims priority under 35 U.S.C. § 119 to Japanese Patent Application No. 2015-219041, filed on Nov. 9, 2015. The above application is hereby expressly incorporated by reference, in its entirety, into the present application.

BACKGROUND OF THE INVENTION

Field of the Invention

The present invention relates to an ultrasonic endoscope, and particularly relates to an ultrasonic endoscope including an ultrasonic observation unit provided to a distal end part body of an insertion unit, and a method of manufacturing the same.

Description of the Related Art

Japanese Patent Application Laid-Open No. 2013-27695 discloses an ultrasonic observation device (ultrasonic endoscope) including an ultrasonic communication unit (ultrasonic observation unit) provided to a distal end part of an insertion unit inserted into the inside of a body.

The ultrasonic communication unit of Japanese Patent Application Laid-Open No. 2013-27695 is provided with a plurality of piezoelectric elements arrayed in a convex circular arc shape. The surface of the piezoelectric element functions as an observation surface through which ultrasonic waves are communicated. An acoustic lens for converging an ultrasonic beam is provided on the top surface of the observation surface through an acoustic matching layer. A backing material is provided on the bottom surface of the observation surface of the piezoelectric element.

Each piezoelectric element is provided with an electrode, and the electrode is connected with a wiring connection unit through a flexible printed board. Typically, the wiring connection unit is provided on the bottom surface of the backing material. The wiring connection unit is connected with a plurality of wires for supplying a drive voltage to the respective piezoelectric elements. These wires are housed in a wire housing space provided to an ultrasonic-oscillator housing part housing an ultrasonic oscillator. The wire housing space is provided on a side on which the bottom surface of the ultrasonic oscillator is housed. In the present specification, the ultrasonic oscillator also refers to the piezoelectric elements and the backing material, and the bottom surface of the ultrasonic oscillator refers to the bottom surface of the backing material.

Japanese Patent Application Laid-Open No. 2013-27695 discloses that the acoustic lens is bonded to the ultrasonic communication unit (ultrasonic oscillator), and the ultrasonic communication unit to which the acoustic lens is bonded is assembled to a holding unit (ultrasonic-oscillator housing part) provided to the distal end part of the insertion unit.

SUMMARY OF THE INVENTION

The plurality of wires housed in the wire housing space of the ultrasonic-oscillator housing part are fixed to the wire housing space by filling agent that fills the wire housing space so as to avoid breaking.

In the technology disclosed in Japanese Patent Application Laid-Open No. 2013-27695, when the ultrasonic communication unit is assembled to the holding unit (ultrasonic-oscillator housing part), a gap formed between the ultrasonic communication unit and the holding unit is filled with sealing agent so as to prevent liquid from flowing into the inside of the holding unit (achieve liquid-tightness).

However, in the technology disclosed in Japanese Patent Application Laid-Open No. 2013-27695, when the sealing agent that fills the gap formed between the ultrasonic communication unit and the holding unit flows into the wire housing space, the filling agent to fix the wires insufficiently fills the wire housing space, which makes it difficult to sufficiently fix the wires.

The present invention is intended to solve such a problem, and it is an object of the present invention to provide an ultrasonic endoscope in which wiring can be reliably fixed in a wire housing space of an ultrasonic-oscillator housing part, and a method of manufacturing the ultrasonic endoscope.

To achieve the object of the present invention, an ultrasonic endoscope according to the present invention includes: an insertion unit inserted into an inside of the body; a distal end part body provided to a distal end of the insertion unit; an ultrasonic observation unit provided to the distal end part body; an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element; a wiring connection unit provided to the ultrasonic oscillator and connected with wiring for supplying a drive voltage to the ultrasonic oscillator; an ultrasonic-oscillator housing part covering the side surfaces and the bottom surface of the ultrasonic oscillator, housing the ultrasonic oscillator, and including a wire housing space in which the wiring is housed, on a side on which the bottom surface of the ultrasonic oscillator is housed; an acoustic lens made of resin covering the observation surface of the ultrasonic oscillator and adhered to the ultrasonic-oscillator housing part; and a sealing member that seals a gap formed between the ultrasonic oscillator and the ultrasonic-oscillator housing part.

According to the present invention, the wire housing space is encapsulated from the outside by sealing the gap formed between the ultrasonic oscillator and the ultrasonic-oscillator housing part by the sealing member. With this configuration, the wire housing space can be sufficiently filled with filling agent for fixing the wiring to the wire housing space. This achieves an ultrasonic endoscope in which the wiring can be reliably fixed to the wire housing space of the ultrasonic-oscillator housing part.

In an aspect of the present invention, it is preferable that the sealing member is provided between the side surfaces of the ultrasonic oscillator and the ultrasonic-oscillator housing part.

According to the aspect of the present invention, the wire housing space can be encapsulated from the outside by the sealing member provided between the side surfaces of the ultrasonic oscillator and the ultrasonic-oscillator housing part.

In another aspect of the present invention, it is preferable that the sealing members are provided between the ultrasonic-oscillator housing part and two side surfaces parallel to a longitudinal axis of the insertion unit and facing to each other among the side surfaces of the ultrasonic oscillator and are provided between the ultrasonic-oscillator housing part and two side surfaces intersecting with the longitudinal axis of the insertion unit and facing to each other among the side surfaces of the ultrasonic oscillator.

In another aspect of the present invention, it is preferable that the sealing member has a uniform thickness in a normal direction of a surface of the sealing member, which is in contact with a corresponding one of the side surfaces of the ultrasonic oscillator when the ultrasonic oscillator is housed in the ultrasonic-oscillator housing part.

In another aspect of the present invention, it is preferable that the sealing member is elastic in a thickness direction corresponding to the normal direction.

In another aspect of the present invention, it is preferable that the sealing member is provided between the bottom surface of the ultrasonic oscillator and the ultrasonic-oscillator housing part.

According to the aspect of the present invention, the wire housing space can be encapsulated from the outside by the sealing member provided between the bottom surface of the ultrasonic oscillator and the ultrasonic-oscillator housing part.

In another aspect of the present invention, it is preferable that the wiring connection unit is provided to the bottom surface of the ultrasonic oscillator.

In another aspect of the present invention, it is preferable that the wiring connection unit is provided in a central part of the bottom surface, and the sealing member is provided in a peripheral part of the bottom surface.

According to the aspect of the present invention, the acoustic lens is assembled to the ultrasonic oscillator by bonding a previously manufactured acoustic lens to the ultrasonic oscillator, or by loading the ultrasonic oscillator into a mold while the ultrasonic oscillator is housed in the ultrasonic-oscillator housing part, and injecting melted resin to be formed as an acoustic lens into the mold.

In the latter method, it is preferable that the resin is thermoplastic resin. The fluid melted thermoplastic resin injected into the mold is prevented from flowing into the wire housing space by the sealing member, and thus the wire housing space can be sufficiently filled with filling agent for fixing wiring in the wire housing space.

To achieve the object of the present invention, a method of manufacturing an ultrasonic endoscope according to the present invention is a method of manufacturing an ultrasonic endoscope including: an insertion unit inserted into an inside of the body; a distal end part body provided to a distal end of the insertion unit; an ultrasonic observation unit provided to the distal end part body; an ultrasonic oscillator provided to the ultrasonic observation unit and including an observation surface through which ultrasonic waves are communicated, side surfaces adjacent to the observation surface, a bottom surface opposite to the observation surface, a piezoelectric element provided closer to the observation surface, and a backing material provided to the bottom surface of the piezoelectric element; a wiring connection unit provided to the ultrasonic oscillator and connected with wiring for supplying a drive voltage to the ultrasonic oscillator; and an ultrasonic-oscillator housing part covering the side surfaces and the bottom surface of the ultrasonic oscillator, housing the ultrasonic oscillator, and including a wire housing space in which the wiring is housed, on a side on which the bottom surface of the ultrasonic oscillator is housed. The method includes: housing the ultrasonic oscillator in the ultrasonic-oscillator housing part and sealing a gap formed between the ultrasonic oscillator and the ultrasonic-oscillator housing part with the sealing member; and shaping an acoustic lens on the observation surface of the ultrasonic oscillator with fluid resin and filling the gap between the ultrasonic oscillator and the ultrasonic-oscillator housing part with the resin while the gap is sealed by the sealing member.

The present invention provides an ultrasonic endoscope in which wiring can be reliably fixed to a wire housing space of an ultrasonic-oscillator housing part, and a method of manufacture the ultrasonic endoscope.

DETAILED DESCRIPTION OF THE PREFERRED EMBODIMENTS

Preferable embodiments of an ultrasonic endoscope according to the present invention and a method of manufacturing the ultrasonic endoscope will be described below in detail with reference to the accompanying drawings.

Figure 1:
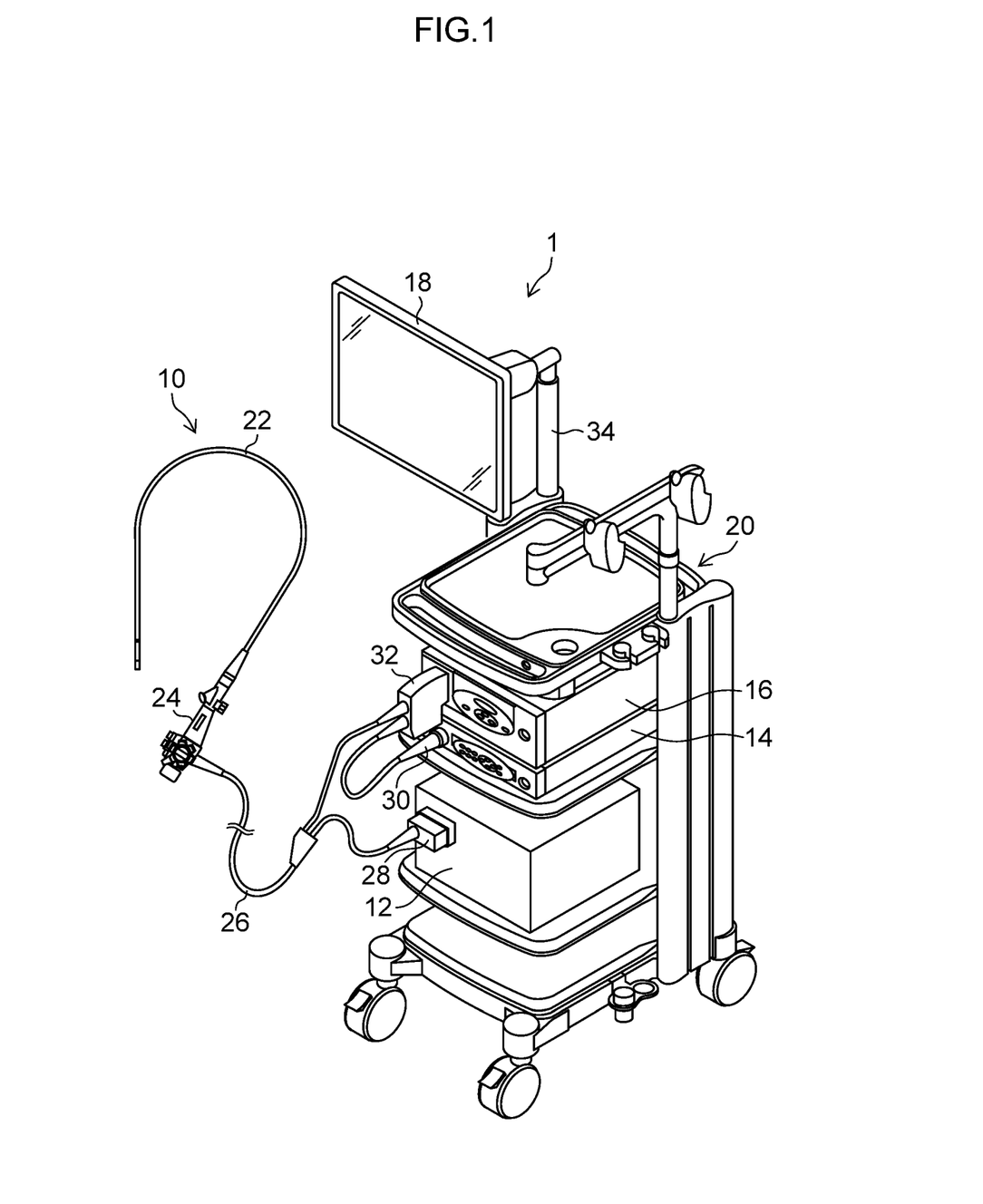
FIG. 1 is an entire configuration diagram of an ultrasonic examination system including an ultrasonic endoscope according to an embodiment.
Figure 2:
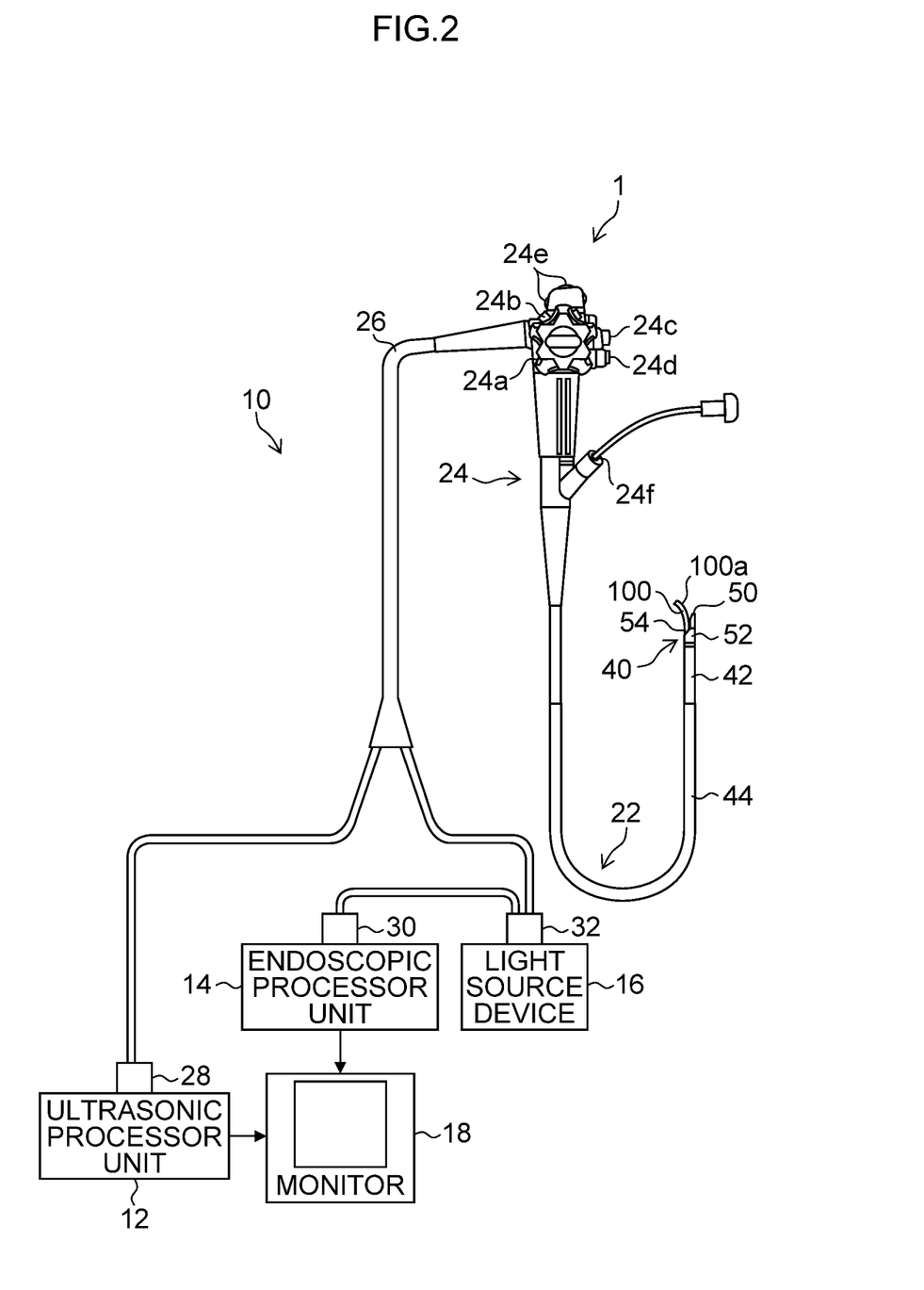
FIG. 2 is a block diagram illustrating the entire configuration of the ultrasonic examination system in FIG. 1.

FIG. 1 is an entire configuration diagram of an ultrasonic examination system 1 including an ultrasonic endoscope 10 according to the present embodiment. FIG. 2 is a block diagram of the entire configuration of the ultrasonic examination system 1 illustrated in FIG. 1.

[Ultrasonic Examination System 1]

The ultrasonic examination system 1 includes the ultrasonic endoscope 10 that captures an endoscopic image and an ultrasonic image of the inside of the body, an ultrasonic processor unit 12 that generates an ultrasonic image, an endoscopic processor unit 14 that generates an endoscopic image, a light source device 16 that supplies the ultrasonic endoscope 10 with illumination light that illuminates the inside of the body, and a monitor 18 that displays an endoscopic image and an ultrasonic image thereon.

[Ultrasonic Endoscope 10]

The ultrasonic endoscope 10 is a convex ultrasonic endoscope including an insertion unit 22 inserted into the inside of the body, an operating unit 24 provided continuously with a proximal end of the insertion unit 22, and a universal cord 26 a proximal end of which is connected with the operating unit 24. A distal end of the universal cord 26 is provided with a connector 28 connected with the ultrasonic processor unit 12, a connector 30 connected with the endoscopic processor unit 14, and a connector 32 connected with the light source device 16. The ultrasonic endoscope 10 is detachably connected with the ultrasonic processor unit 12, the endoscopic processor unit 14, and the light source device 16 through the respective connectors 28, 30, and 32.

The ultrasonic processor unit 12, the endoscopic processor unit 14, and the light source device 16 are loaded on a cart 20 with casters as illustrated in FIG. 1 and integrally moved. The monitor 18 is supported by a support 34 of the cart 20. The direction and height of a screen of the monitor 18 are adjusted through a rotation mechanism and a height adjusting mechanism (not illustrated) provided to the support 34.

<Insertion Unit 22>

As illustrated in FIG. 2, the insertion unit 22 includes a distal end rigid part 40 including a distal end part body 70 (refer to FIG. 3) made of a rigid material, a curved part 42 provided continuously with a proximal end side of the distal end rigid part 40, and a flexible part 44 having flexibility and a small diameter and a long length and coupling a proximal end side of the curved part 42 and a distal end of the operating unit 24, in this order from its distal end. In other words, the distal end of the insertion unit 22 is provided with the distal end part body 70. A surgical-tool guide opening 54 to be described later is formed in the distal end part body 70 (refer to FIG. 3).

Figure 3:
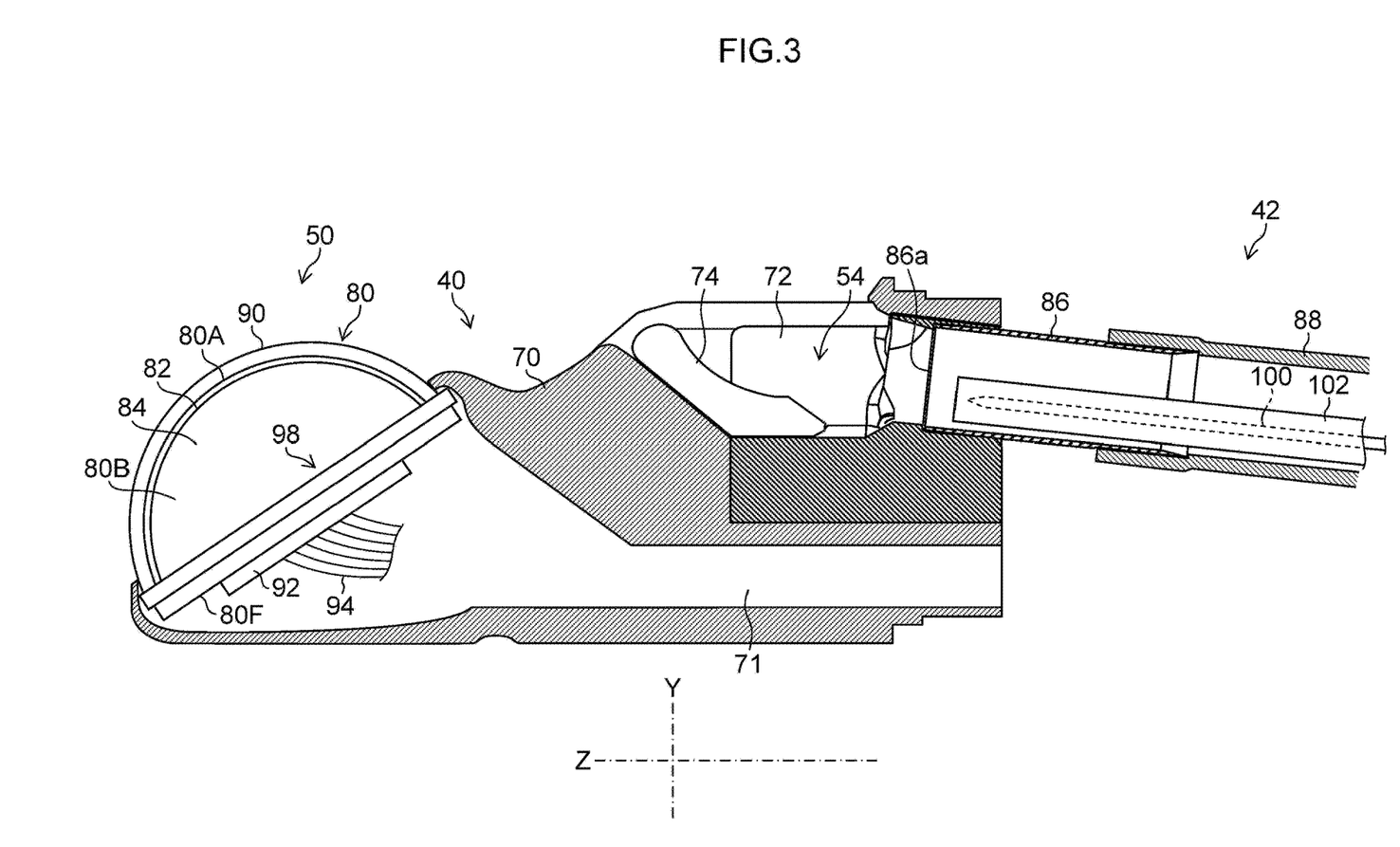
FIG. 3 is an enlarged sectional view illustrating a main part of a distal end structure of an insertion unit of the ultrasonic endoscope illustrated in FIG. 1.

FIG. 3 is a main-part enlarged sectional view illustrating a non-angled state of the insertion unit 22 of the ultrasonic endoscope 10 illustrated in FIG. 1.

A surgical-tool insertion tube 88 is arranged inside of the insertion unit 22 so as to guide a surgical tool including a puncture needle 100 and a sheath 102 to the surgical-tool guide opening 54. A proximal end of the surgical-tool insertion tube 88 is connected with a surgical-tool insertion opening 24f provided to the operating unit 24 illustrated in FIG. 2, whereas a distal end thereof is connected with a proximal end of a connecting pipe 86 (refer to FIG. 3) arranged at a coupling position of the distal end rigid part 40 and the curved part 42. The connecting pipe 86 is made of metal such as stainless steel, mounted on the distal end part body 70 such that a distal end thereof is communicated with the surgical-tool guide opening 54. The surgical-tool insertion tube 88 is made of, for example, polytetrafluoroethylene (PTFE).

As illustrated in FIG. 2, the distal end part body 70 (refer to FIG. 3) of the distal end rigid part 40 is provided with an ultrasonic observation unit 50, an endoscope observation unit 52, and the surgical-tool guide opening 54.

The ultrasonic observation unit 50 includes an ultrasonic oscillator including an observation surface through which ultrasonic waves are communicated as described later. The ultrasonic observation unit 50 acquires an ultrasonic signal for generating as an ultrasonic image, a topographic image of cellular tissue existing deeper than a wall of the body cavity.

The endoscope observation unit 52 includes, for example, components of an observation optical system and an illumination optical system and an image pickup element and a peripheral circuit thereof as described later. The endoscope observation unit 52 optically captures the surface of a wall of the body cavity so as to acquire an image signal for displaying an endoscopic image for observation.

As illustrated in FIG. 3, the surgical-tool guide opening 54 guides, into the inside of the body, a distal end (a distal end 100a of the puncture needle 100 in FIG. 2) of the surgical tool including the puncture needle 100 and the sheath 102 inserted into the surgical-tool insertion tube 88. The surgical-tool guide opening 54 is communicated with a distal end of the connecting pipe 86, and an elevator 74 that changes a direction in which the puncture needle 100 is guided is provided closer to the distal end of the connecting pipe 86.

Although embodiment exemplarily describes the surgical tool including the puncture needle 100 and the sheath 102, the present invention is not limited thereto but is applicable to other surgical tools such as forceps.

<Operating Unit 24>

As illustrated in FIG. 2, the operating unit 24 includes, for example, an angle knob 24a for curving the curved part 42 of the insertion unit 22 vertically and horizontally, an elevation lever 24b for standing up the elevator 74 (refer to FIG. 3), a suction button 24c for performing suction, an insufflation button 24d for performing air and water supply, and a plurality of operation members 24e for performing display switching of the monitor and instructions to freeze and release a display image. The surgical-tool insertion opening 24f for inserting various surgical tools into the surgical-tool insertion tube 88 (refer to FIG. 3) is provided as an extension closer to the distal end of the operating unit 24.

<Processor Unit and the Like>

The ultrasonic processor unit 12 transmits ultrasonic waves at a predetermined frequency from the observation surface toward an observation object by driving a piezoelectric element (to be described later) included in the ultrasonic observation unit 50. Then, the ultrasonic processor unit 12 receives, through the observation surface, ultrasonic waves reflected from the observation object and acquires, from the ultrasonic observation unit 50, an electric signal (ultrasonic signal) obtained from the received ultrasonic waves, and generates an image signal for an ultrasonic image by performing various kinds of signal processing on the electric signal.

The endoscopic processor unit 14 acquires the image signal transmitted from the image pickup element of the endoscope observation unit 52 of the ultrasonic endoscope 10 by performing drive control of the image pickup element, and generates an image signal for an endoscopic image by performing various kinds of signal processing on the image signal.

The light source device 16 supplies the illumination optical system with illumination light to be emitted from the illumination optical system of the distal end rigid part 40 for illuminating an observation view range of the endoscope observation unit 52.

The monitor 18 receives the image signals generated by the ultrasonic processor unit 12 and the endoscopic processor unit 14, and displays an ultrasonic image and an endoscopic image. In the display of these ultrasonic and endoscopic images, each of the images may be displayed on the monitor 18 in a switching manner as appropriate or both of the images may be simultaneously displayed on the monitor 18.

<Distal End Rigid Part 40>

FIGS. 4, 5, 6, and 7 are a perspective view, a plan view, a side view, and a front view of the distal end rigid part 40, respectively.

As illustrated in these diagrams, the distal end part body 70 of the distal end rigid part 40 is provided with the ultrasonic observation unit 50, the endoscope observation unit 52, and the surgical-tool guide opening 54 as described above.

<Ultrasonic Observation Unit 50>

As illustrated in FIG. 3, the ultrasonic observation unit 50 is provided to the distal end part body 70. The ultrasonic observation unit 50 is provided with an ultrasonic oscillator 80.

Figure 4:
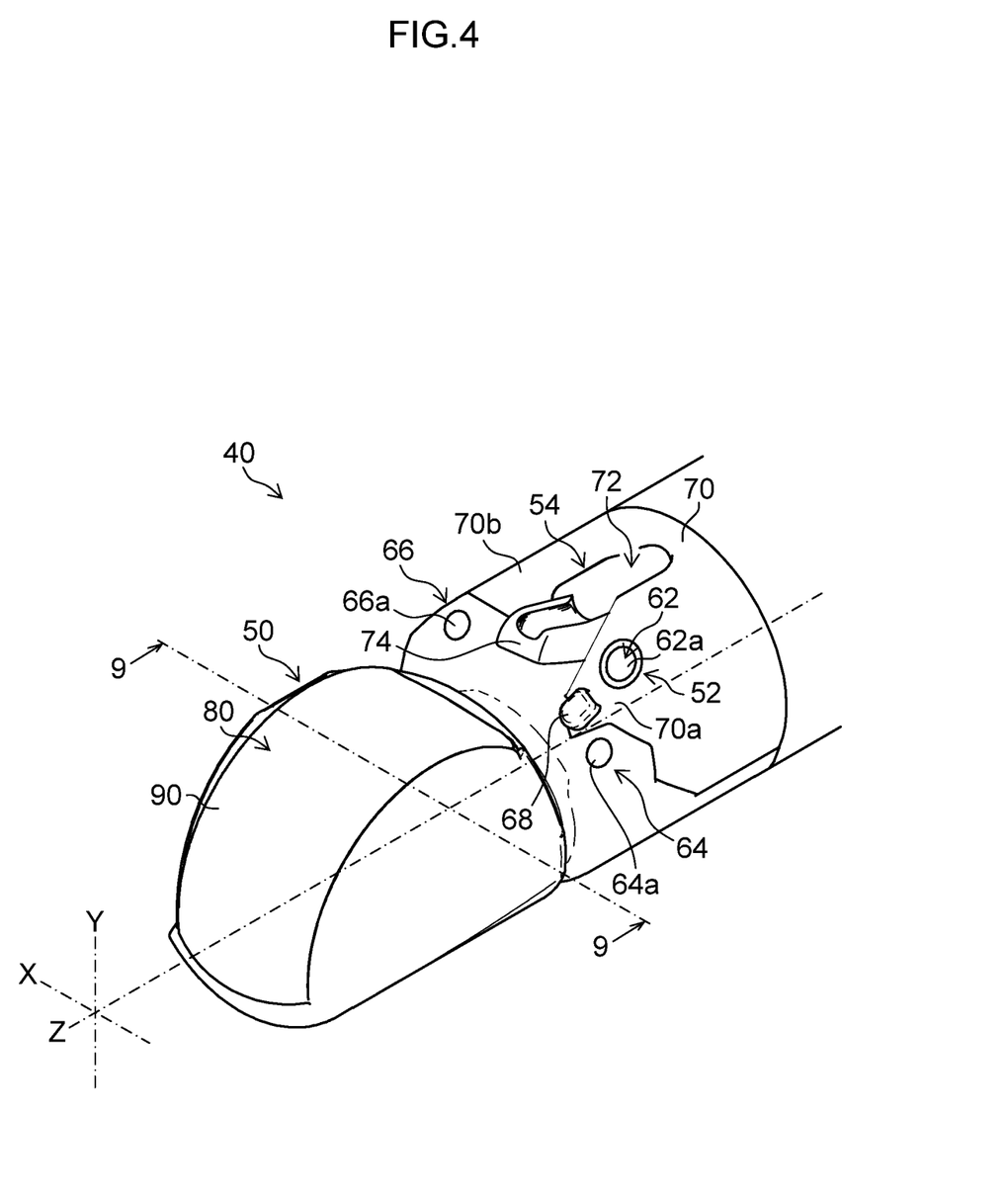
FIG. 4 is a perspective view of a distal end rigid part of the ultrasonic endoscope.
Figure 5:
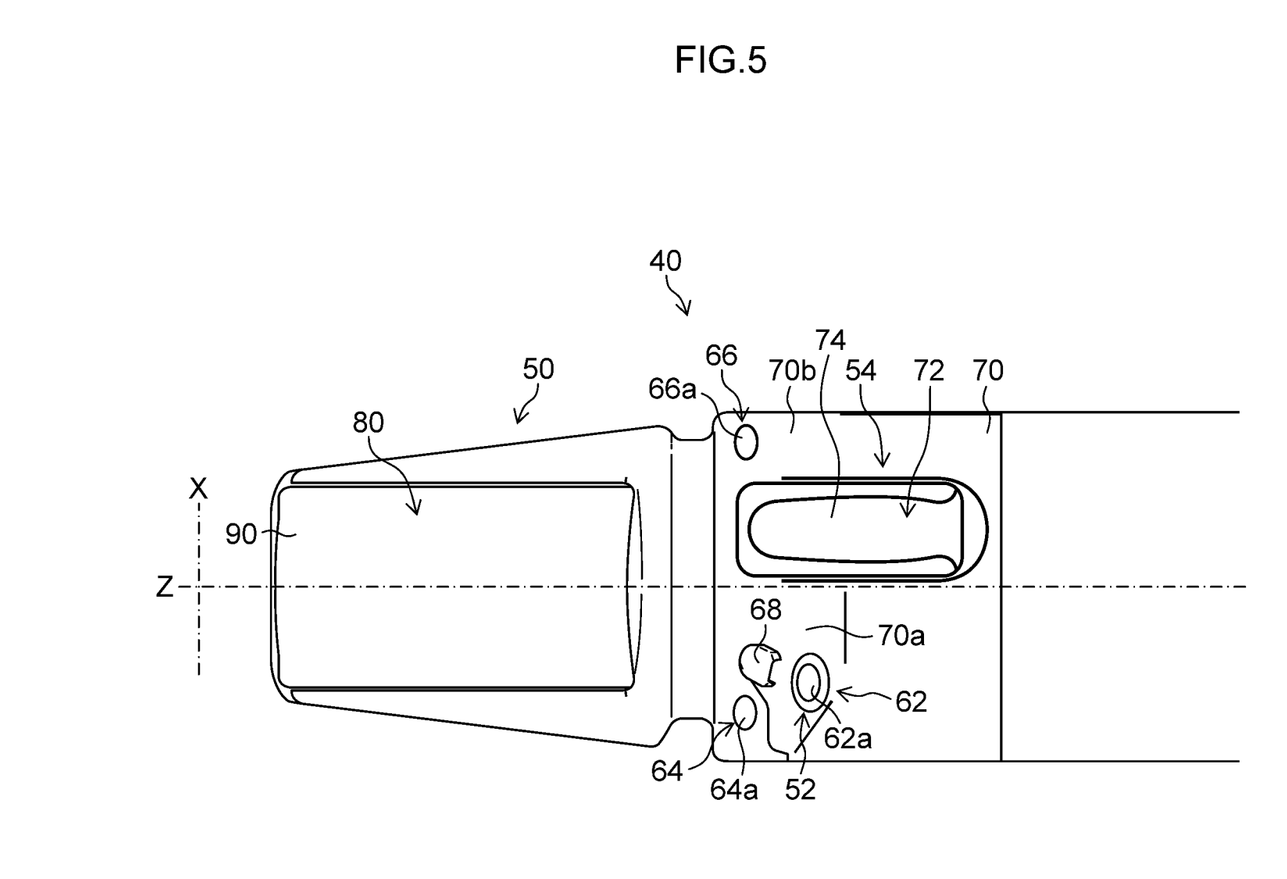
FIG. 5 is a plan view of the distal end rigid part of the ultrasonic endoscope.
Figure 6:
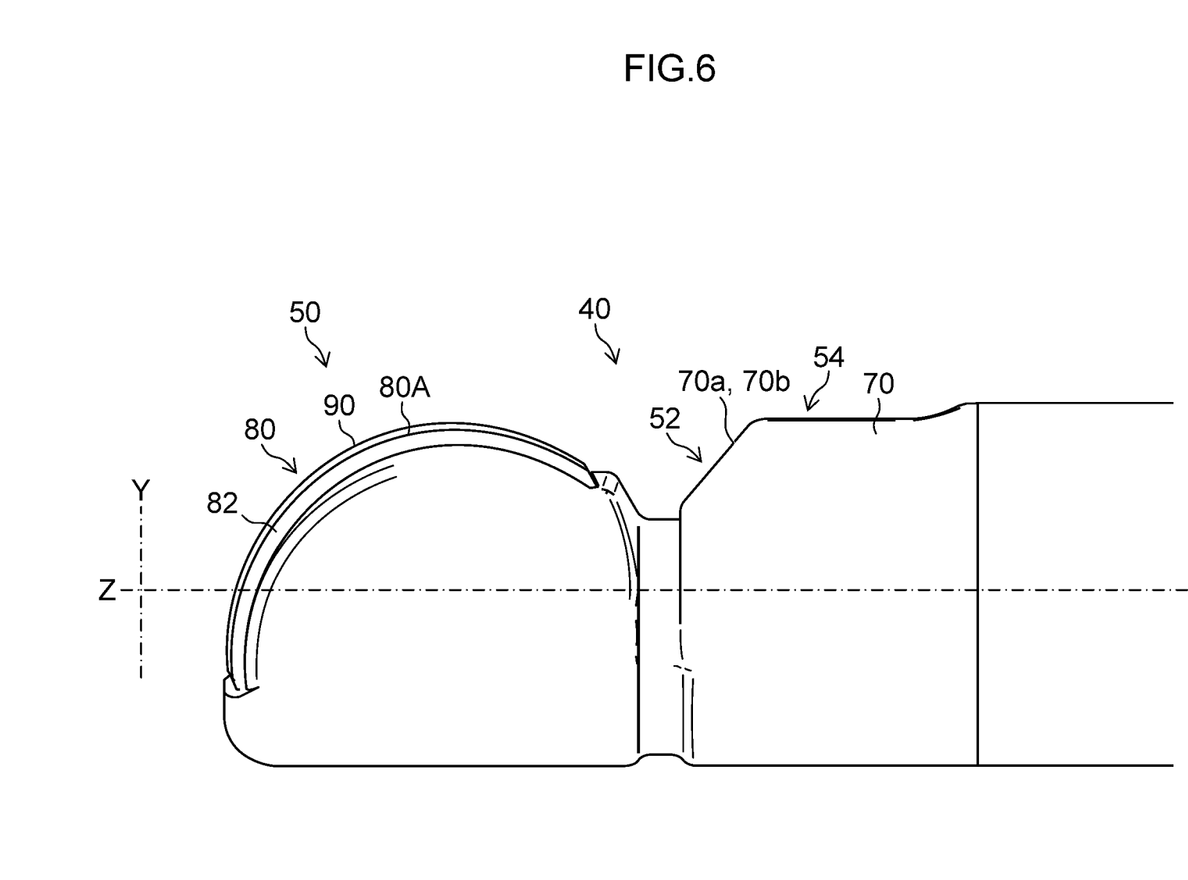
FIG. 6 is a side view of the distal end rigid part of the ultrasonic endoscope.
Figure 7:
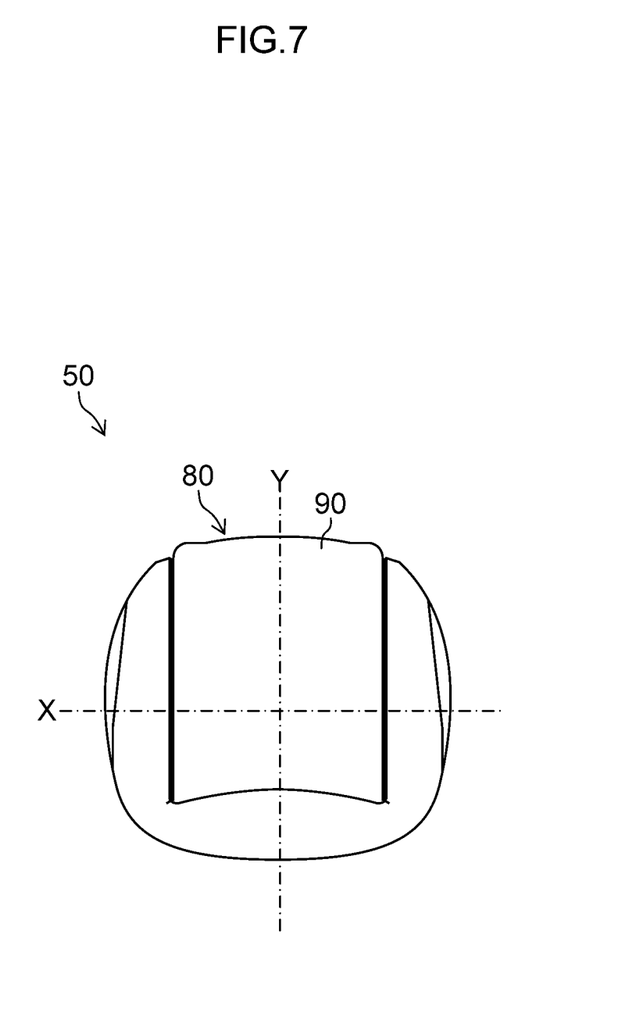
FIG. 7 is a front view of the distal end rigid part of the ultrasonic endoscope.
Figure 8:
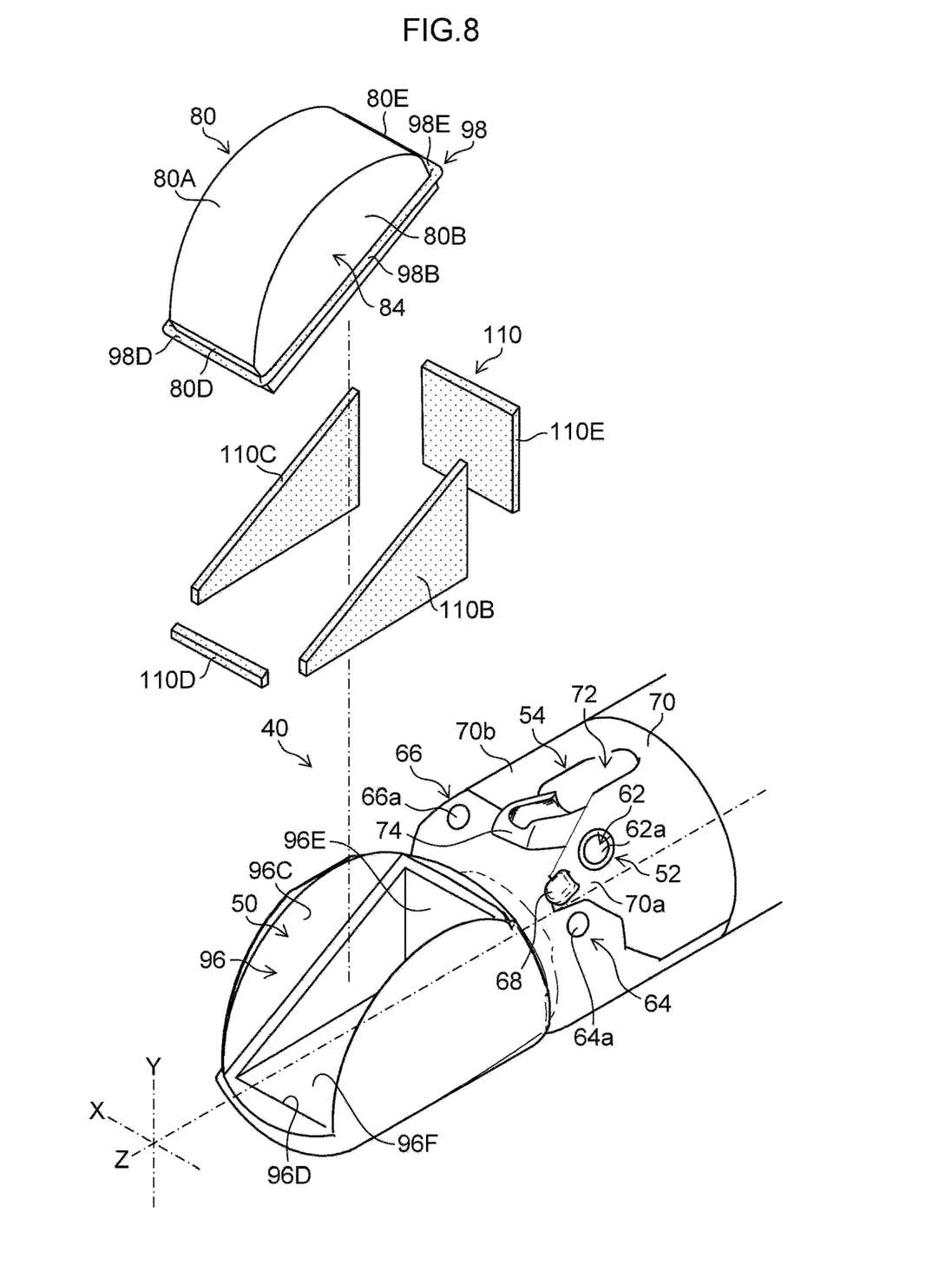
FIG. 8 is a diagram illustrating assembly of an ultrasonic oscillator to the distal end part body.
Figure 9:
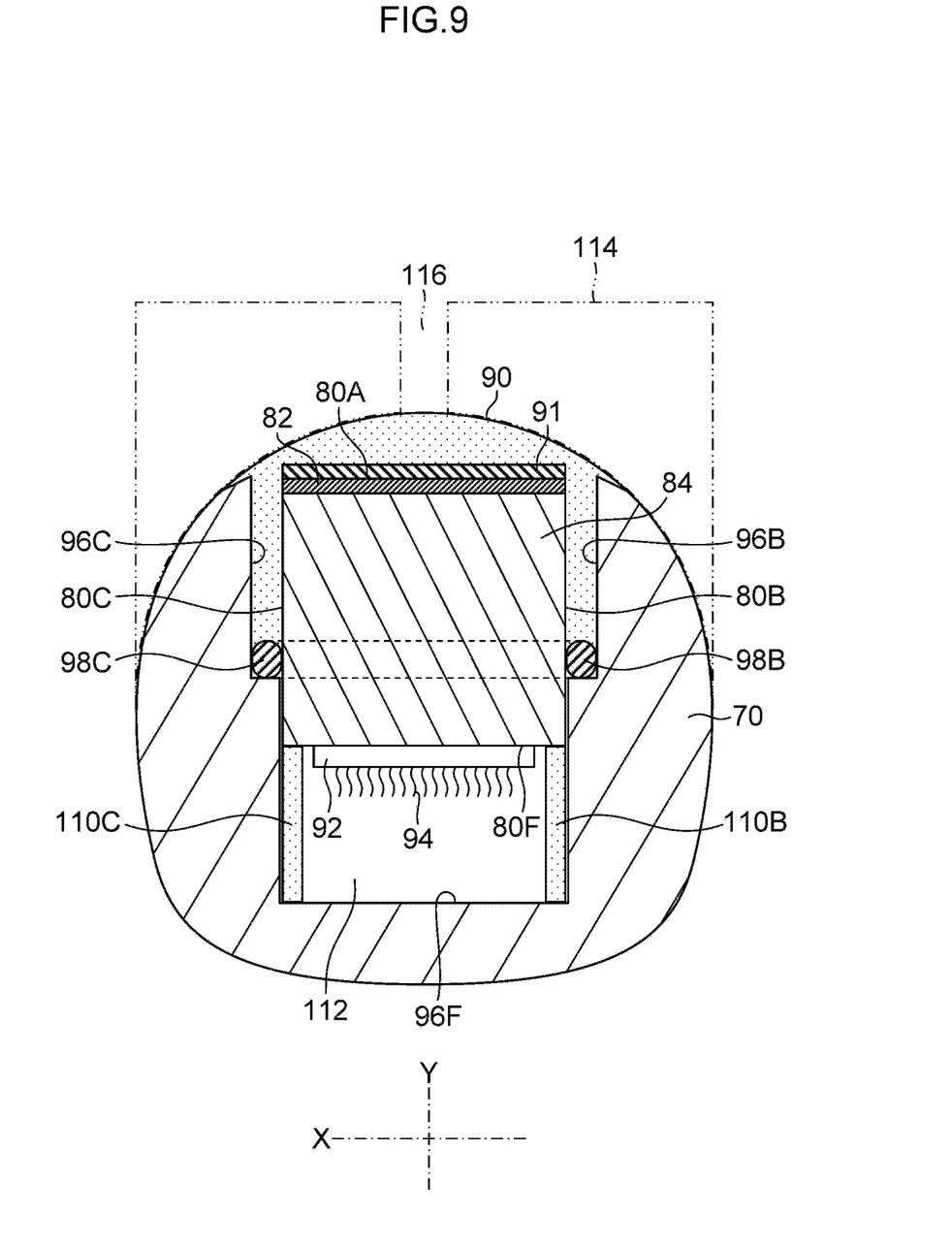
FIG. 9 is a sectional view of the distal end part body and the ultrasonic oscillator taken along line 9-9 in FIG. 4.
Figure 10:
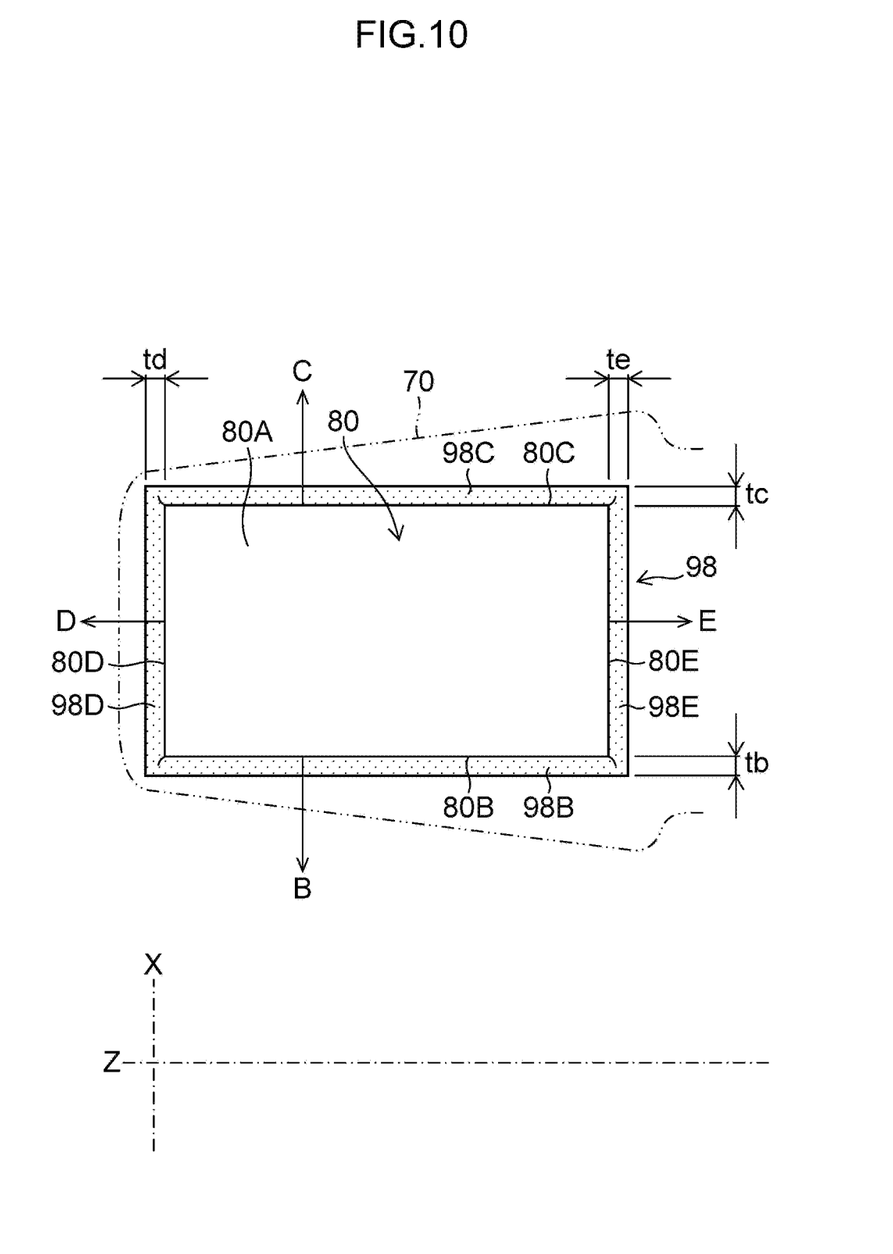
FIG. 10 is a plan view of the ultrasonic oscillator.

FIG. 8 is a diagram illustrating assembly of the ultrasonic oscillator 80 to the distal end part body 70, FIG. 9 is a sectional view of the distal end part body 70 and the ultrasonic oscillator 80 taken along line 9-9 in FIG. 4, and FIG. 10 is a plan view of the ultrasonic oscillator 80.

As illustrated in these diagrams, the ultrasonic oscillator 80 includes an observation surface 80A through which ultrasonic waves are communicated, four side surfaces 80B, 80C, 80D, and 80E adjacent to the observation surface 80A, a bottom surface 80F opposite to the observation surface 80A, a plurality of plate piezoelectric elements 82 provided closer to the observation surface 80A, and a backing material 84 provided to the bottom surfaces of the plurality of piezoelectric elements 82. The four side surfaces are side surfaces of the backing material 84 formed in a semi-cylinder. Among the side surfaces, the side surfaces 80B and 80C are two side surfaces parallel to a longitudinal axis Z of the insertion unit 22 and facing to each other, and the side surfaces 80D and 80E are two side surfaces intersecting with the longitudinal axis Z of the insertion unit 22 and facing to each other.

The plurality of piezoelectric elements 82 are arrayed in the direction of the longitudinal axis Z of the insertion unit 22. In other words, the plurality of piezoelectric elements 82 are arrayed from a position close to a distal end of the distal end rigid part 40 toward the proximal end side of the distal end rigid part 40, and their surfaces serve as the observation surface 80A through which ultrasonic waves are communicated. The observation surface 80A is shaped as an arc surface in the direction of the longitudinal axis Z, but is not limited to this shape, and may be shaped as a curved surface having a plurality of different curvatures. The observation surface 80A is provided, through an acoustic matching layer 91 (refer to FIG. 9), with an acoustic lens 90 for converging ultrasonic waves.

The plurality of piezoelectric elements 82 are each provided with an electrode (not illustrated), and the electrode is connected with a wiring connection unit 92 in FIG. 9 through a flexible printed board (not illustrated). The wiring connection unit 92 is provided in a central part of the bottom surface 80F of the ultrasonic oscillator 80, which is formed in a rectangle. The wiring connection unit 92 is connected with a plurality of narrow wires 94 for supplying a drive voltage to the plurality of piezoelectric elements 82, and these wires 94 are inserted into a wiring insertion hole 71 (refer to FIG. 3) of the distal end part body 70 and connected with the connector 28 in FIG. 2.

The ultrasonic observation unit 50 can perform ultrasonic electron scanning by supplying a drive voltage from the ultrasonic processor unit 12 to the plurality of piezoelectric elements 82 to sequentially drive the plurality of piezoelectric elements 82.

In FIGS. 3 to 10, an X axis is defined to be a horizontal axis in a transverse direction orthogonal to the longitudinal axis Z, and a Y axis is defined to be a vertical axis in the vertical direction.

The distal end part body 70 is provided with an ultrasonic-oscillator housing part 96 with an opening upper part as illustrated in FIG. 8. The ultrasonic-oscillator housing part 96 includes side surfaces 96B (refer to FIG. 9), 96C, 96D, and 96E and a bottom surface 96F covering the side surfaces 80B, 80C, 80D, and 80E and the bottom surface 80F of the ultrasonic oscillator 80, thereby housing the ultrasonic oscillator 80.

A sealing member 98 is provided between the side surfaces 80B, 80C, 80D, and 80E of the ultrasonic oscillator 80 and the side surfaces 96B, 96C, 96D, and 96E of the ultrasonic-oscillator housing part 96.

[Sealing Member 98]

The sealing member 98 is a frame member formed as an integration of the four sealing members 98B, 98C, 98D, and 98E. The sealing member 98B is provided between the side surface 80B of the ultrasonic oscillator 80 and the side surface 96B of the ultrasonic-oscillator housing part 96, the sealing member 98C is provided between the side surface 80C of the ultrasonic oscillator 80 and the side surface 96C of the ultrasonic-oscillator housing part 96, the sealing member 98D is provided between the side surface 80D of the ultrasonic oscillator 80 and the side surface 96D of the ultrasonic-oscillator housing part 96, and the sealing member 98E is provided between the side surface 80E of the ultrasonic oscillator 80 and the side surface 96E of the ultrasonic-oscillator housing part 96.

In other words, a gap between the side surface 80B of the ultrasonic oscillator 80 and the side surface 96B of the ultrasonic-oscillator housing part 96 is sealed by the sealing member 98B, a gap between the side surface 80C of the ultrasonic oscillator 80 and the side surface 96C of the ultrasonic-oscillator housing part 96 is sealed by the sealing member 98C, a gap between the side surface 80D of the ultrasonic oscillator 80 and the side surface 96D of the ultrasonic-oscillator housing part 96 is sealed by the sealing member 98D, and a gap between the side surface 80E of the ultrasonic oscillator 80 and the side surface 96E of the ultrasonic-oscillator housing part 96 is sealed by the sealing member 98E.

Although the present embodiment describes the example in which the sealing member 98 is provided to the ultrasonic oscillator 80, the sealing member 98 may be provided to the ultrasonic-oscillator housing part 96.

It is preferable that when the ultrasonic oscillator 80 is housed in the ultrasonic-oscillator housing part 96, the sealing member 98 having the above-described configuration has uniform thicknesses tb, tc, td, and te measured in directions (indicated by arrows B, C, D, and E) normal to surfaces of the sealing member 98, which are in contact with the side surfaces 80B, 80C, 80D, and 80E of the ultrasonic oscillator 80 as illustrated in FIG. 10.

It is preferable that the sealing member 98 is made of resin or rubber elastic in a thickness direction corresponding to each normal direction described above, and it is more preferable that the sealing member 98 is made of a thermoplastic resin material such as silicone, which is the same as that of the acoustic lens 90.

[Sealing Member 110]

As illustrated in FIGS. 8 and 9, a sealing member 110 is provided between the bottom surface 80F of the ultrasonic oscillator 80 and the bottom surface 96F of the ultrasonic-oscillator housing part 96.

The sealing member 110 includes four sealing members 110B, 110C, 110D, and 110E. The sealing member 110B supports part of the bottom surface 96F of the ultrasonic-oscillator housing part 96, which corresponds to the side surface 80B of the ultrasonic oscillator 80, the sealing member 110C supports part of the bottom surface 96F of the ultrasonic-oscillator housing part 96, which corresponds to the side surface 80C of the ultrasonic oscillator 80, the sealing member 110D supports part of the bottom surface 96F of the ultrasonic-oscillator housing part 96, which corresponds to the side surface 80D of the ultrasonic oscillator 80, and the sealing member 110E supports part of the bottom surface 96F of the ultrasonic-oscillator housing part 96, which corresponds to the side surface 80E of the ultrasonic oscillator 80. In other words, the sealing member 110 is provided in a peripheral part of the bottom surface 80F.

The ultrasonic oscillator 80 is housed in the ultrasonic-oscillator housing part 96 with its distal end being tilted downward, and thus the sealing members 110B and 110C are each formed in a triangle, the sealing member 110D is formed in a rectangle, and the sealing member 110E is formed in a rectangle having a height larger than that of the sealing member 110D.

The sealing member 110 provides a wire housing space 112 in which the wires 94 are housed, between the bottom surface 80F of the ultrasonic oscillator 80 and the bottom surface 96F of the ultrasonic-oscillator housing part 96. In other words, the ultrasonic-oscillator housing part 96 includes the wire housing space 112 in which the wires 94 is housed, on a side on which the bottom surface 80F of the ultrasonic oscillator 80 is housed.

The sealing members 98 and 110 prevent melted thermoplastic resin of the acoustic lens 90 from flowing into the wire housing space 112 at formation of the acoustic lens 90 to be described later.

Similarly to the sealing member 98, it is preferable that the sealing member 110 is made of elastic resin or rubber, and it is more preferable that the sealing member 110 is made of a material such as silicone, which is the same as that of the acoustic lens 90.

[Acoustic Lens 90]

The acoustic lens 90 covers the observation surface 80A of the ultrasonic oscillator 80 and the sealing member 98 and is adhered to the ultrasonic-oscillator housing part 96. A method of assembling the ultrasonic oscillator 80 to the ultrasonic-oscillator housing part 96 will be described later.

<<Endoscope Observation Unit 52>>

The endoscope observation unit 52 includes, for example, an observation optical system 62, illumination optical systems 64 and 66, and an image pickup element (not illustrated), and is provided to the distal end part body 70 on a proximal end side of the ultrasonic observation unit 50, avoiding the surgical-tool guide opening 54.

In the distal end part body 70, tilted surfaces 70a and 70b tilted at a predetermined angle with respect to a plane orthogonal to the longitudinal axis Z are provided at positions closer to the distal end than the surgical-tool guide opening 54 on both sides of the surgical-tool guide opening 54 in the traverse direction. An observation window 62a of the observation optical system 62 and an illumination window 64a of the illumination optical system 64 are arranged on the tilted surface 70a on the left side in the direction from the proximal end side toward the distal end side. An illumination window 66a of the illumination optical system 66 is arranged on the tilted surface 70b on the right side in the direction from the proximal end side toward the distal end side.

The observation optical system 62 includes an optical system member (not illustrated) that takes in light from an object in the observation view range through the observation window 62a and images an object image inside of the distal end rigid part 40. An image pickup element (not illustrated) that captures the object image imaged by the observation optical system 62 and generates an image signal is arranged inside of the distal end rigid part 40.

The illumination optical systems 64 and 66 each include an optical system member that emits illumination light transmitted from the light source device 16 (refer to FIG. 2) through a light guide, to the observation view range through the illumination windows 64a and 66a in a diffusive manner.

A cleaning nozzle 68 that sprays liquid and gas toward the observation window 62a is provided near the observation window 62a on the tilted surface 70a.

<<Surgical-Tool Guide Opening 54>>

The surgical-tool guide opening 54 includes a concave elevator housing part 72 provided on the proximal end side of the ultrasonic observation unit 50 and communicated with an opening 86a of the connecting pipe 86 in FIG. 3. The elevator 74, which changes the direction of guiding the puncture needle 100 guided through the opening 86a of the connecting pipe 86 from the surgical-tool guide opening 54, is rotatably provided to the elevator housing part 72.

The elevator 74 is coupled with a shaft provided to a lever (not illustrated). The lever is rotatably provided to the distal end part body 70 through the shaft and is coupled with a distal end of an operation wire (not illustrated), and a proximal end of the operation wire is coupled with the elevation lever 24b (refer to FIG. 2) of the operating unit 24. With this configuration, when the operation wire is pushed or pulled by operating the elevation lever 24b, the elevator 74 is rotated along with the lever through the shaft so as to change an angle at which the elevator 74 stands up.

Accordingly, the puncture needle 100 guided through the opening 86a of the connecting pipe 86 is guided in a predetermined guide direction along the elevator 74 to the outside through the surgical-tool guide opening 54.

[Method of Assembling the Ultrasonic Oscillator 80 to the Ultrasonic-Oscillator Housing Part 96]

In the present embodiment, after the ultrasonic oscillator 80 to which the acoustic lens 90 is not provided is housed in the ultrasonic-oscillator housing part 96 of the distal end part body 70, the distal end part body 70 is loaded into a mold 114 (refer to FIG. 9), and then fluid melted resin (silicone resin) to be formed into the acoustic lens 90 through solidification is injected into the mold 114.

Figure 11:
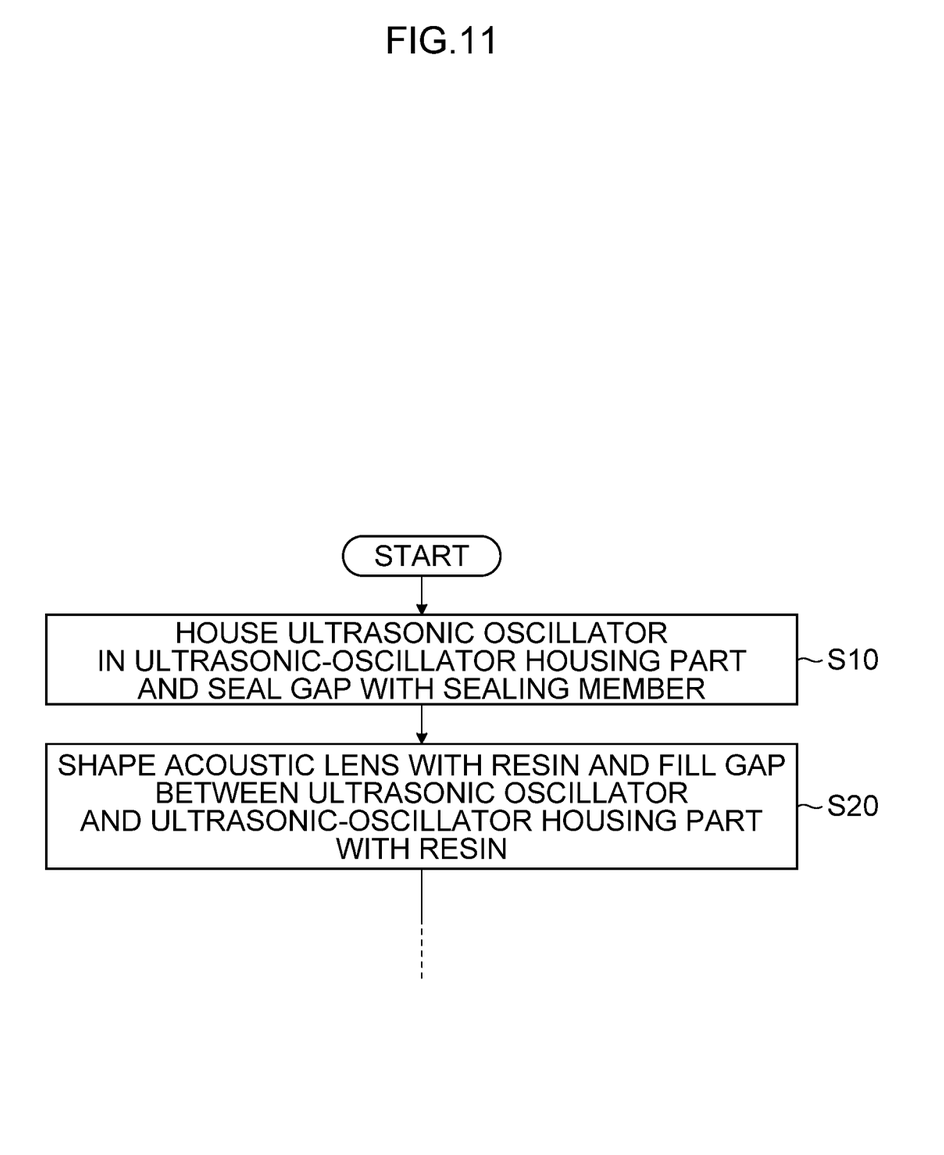
FIG. 11 is a flowchart of a method of manufacturing an ultrasonic endoscope according to the present embodiment.

FIG. 11 is a flowchart of a method of manufacturing the ultrasonic endoscope 10 according to the present embodiment. The method of manufacturing the ultrasonic endoscope 10 according to the present embodiment performs step S10 of housing the ultrasonic oscillator 80 in the ultrasonic-oscillator housing part 96 and sealing a gap formed between the ultrasonic oscillator 80 and the ultrasonic-oscillator housing part 96 with the sealing members 98 and 110. Next, the method performs step S20 of shaping the acoustic lens 90 on the observation surface 80A of the ultrasonic oscillator with fluid resin and filling the gap between the ultrasonic oscillator 80 and the ultrasonic-oscillator housing part 96 with the resin while the gap is sealed by the sealing members 98 and 110.

Specifically, first, the ultrasonic oscillator 80 including the sealing members 98 and 110 is housed in the ultrasonic-oscillator housing part 96 of the distal end part body 70, and the wire housing space 112 is encapsulated from the outside in a liquid-tight manner by the sealing members 98 and 110 (S10). Next, the distal end part body 70 is fixed inside of the mold 114. Next, melted thermoplastic resin (not illustrated) is injected through an injection opening 116 of the mold 114. Next, the mold 114 is placed into a vacuum chamber (not illustrated) to perform defoaming of the melted thermoplastic resin. After the defoaming, the melted thermoplastic resin is injected into the mold 114 again to fill the inside of the mold 114 with the melted thermoplastic resin. Next, a plurality of molds are bonded to the mold so as to form a mold assembly. Next, the mold assembly is placed into a furnace so as to solidify the melted thermoplastic resin (S20). Thereafter, the mold assembly is taken out of the furnace and separated to obtain the distal end part body 70 out of the mold 114. Lastly, any unnecessary burr part around the acoustic lens 90 is removed.

The acoustic lens 90 covering the observation surface 80A of the ultrasonic oscillator 80 and the sealing member 98 and adhered to the ultrasonic-oscillator housing part 96 is shaped in this manner. In other words, in the process of providing the acoustic lens 90 on the observation surface 80A of the ultrasonic oscillator 80, the gap between the ultrasonic oscillator 80 and the ultrasonic-oscillator housing part 96 can be sealed by the acoustic lens 90.

The acoustic lens 90 according to the present embodiment covers the observation surface 80A of the ultrasonic oscillator 80 and the sealing member 98 and is adhered to the ultrasonic-oscillator housing part 96. In other words, in the endoscope observation unit 52 according to the present embodiment, the gap between the ultrasonic oscillator 80 and the ultrasonic-oscillator housing part 96 is sealed by part of the acoustic lens 90 without using sealing agent. Thus, in the endoscope observation unit 52 according to the present embodiment, the part of the acoustic lens 90 provides enhanced liquid-tightness of the ultrasonic observation unit 50 against the distal end part body 70.

[Effect of the Sealing Members 98 and 110]

In the present embodiment, the wire housing space 112 is encapsulated from the outside by sealing the gap formed between the ultrasonic oscillator 80 and the ultrasonic-oscillator housing part 96 in a liquid-tight manner with the sealing members 98 and 110. With this configuration, the wire housing space 112 can be sufficiently filled with filling agent for fixing the wires 94 in the wire housing space 112. This achieves the ultrasonic endoscope 10 in which the wires 94 can be reliably fixed to the wire housing space 112 of the ultrasonic-oscillator housing part 96.

It is preferable that the sealing member 98 according to the present embodiment is provided between the side surfaces 80B to 80E of the ultrasonic oscillator 80 and the ultrasonic-oscillator housing part 96.

With this configuration, the wire housing space 112 can be encapsulated from the outside by the sealing member 98 provided between the side surfaces 80B to 80E of the ultrasonic oscillator 80 and the ultrasonic-oscillator housing part 96.

It is preferable that the sealing member 110 according to the present embodiment is provided between the bottom surface 80F of the ultrasonic oscillator 80 and the ultrasonic-oscillator housing part 96.

With this configuration, the wire housing space 112 can be encapsulated from the outside by the sealing member 110 provided between the bottom surface 80F of the ultrasonic oscillator 80 and the ultrasonic-oscillator housing part 96.

It is preferable that the acoustic lens 90 made of resin according to the present embodiment is made of thermoplastic resin.

With this configuration, the acoustic lens 90 can be shaped by loading the ultrasonic-oscillator housing part 96 into the mold and injecting melted thermoplastic resin to be formed as the acoustic lens 90 into the mold while the ultrasonic oscillator 80 is housed in the ultrasonic-oscillator housing part 96. The fluid melted thermoplastic resin thus injected is prevented from flowing into the wire housing space 112 by the sealing members 98 and 110, and thus the wire housing space 112 can be sufficiently filled with filling agent for fixing the wires 94 in the wire housing space 112.

In the above-described embodiment, the two sealing members 98 and 110 are provided, but at least one sealing member of the two sealing members 98 and 110 may be provided.

In the above-described embodiment, the acoustic lens 90 is formed integrally with the ultrasonic oscillator 80 by the molding technology, but the ultrasonic oscillator may be bonded with a previously manufactured acoustic lens and then assembled to the ultrasonic-oscillator housing part.

What is claimed is:

1. An ultrasonic endoscope comprising:
an insertion unit configured to be inserted into an inside of the body;
a distal end part body provided to a distal end of the insertion unit;
an ultrasonic observation unit provided to the distal end part body;
an ultrasonic oscillator provided to the ultrasonic observation unit and including an observation surface through which ultrasonic waves are communicated, side surfaces adjacent to the observation surface, a bottom surface opposite to the observation surface, a piezoelectric element, and a backing material provided to the bottom surface of the piezoelectric element;
a wiring connection unit provided to the ultrasonic oscillator and connected with wiring for supplying a drive voltage to the ultrasonic oscillator;
an ultrasonic-oscillator housing part covering the side surfaces and the bottom surface of the ultrasonic oscillator, housing the ultrasonic oscillator, and including a wire housing space in which the wiring is housed, on a side on which the bottom surface of the ultrasonic oscillator is housed;
an acoustic lens made of resin covering the observation surface of the ultrasonic oscillator and adhered to the ultrasonic-oscillator housing part; and
a first sealing member that seals a gap formed between the ultrasonic oscillator and the ultrasonic-oscillator housing part, wherein
the acoustic lens has a fixing part which is filled between the side surfaces of the ultrasonic oscillator and the ultrasonic-oscillator housing part, and
the first sealing member is provided in a space defined by an end of the fixing part of the acoustic lens on a side of the bottom surface of the ultrasonic oscillator, the ultrasonic-oscillator housing part and the side surfaces of the ultrasonic oscillator.

2. The ultrasonic endoscope according to claim 1, wherein the first sealing member is provided between the ultrasonic-oscillator housing part and two side surfaces parallel to a longitudinal axis of the insertion unit and facing to each other among the side surfaces of the ultrasonic oscillator and are provided between the ultrasonic-oscillator housing part and two side surfaces intersecting with the longitudinal axis of the insertion unit and facing to each other among the side surfaces of the ultrasonic oscillator.

3. The ultrasonic endoscope according to claim 1, wherein the first sealing member is provided between the ultrasonic-oscillator housing part and two side surfaces parallel to a longitudinal axis of the insertion unit and facing to each other among the side surfaces of the ultrasonic oscillator and are provided between the ultrasonic-oscillator housing part and two side surfaces intersecting with the longitudinal axis of the insertion unit and facing to each other among the side surfaces of the ultrasonic oscillator.

4. The ultrasonic endoscope according to claim 1, wherein the first sealing member has a uniform thickness in a normal direction of a surface of the first sealing member, which is in contact with a corresponding one of the side surfaces of the ultrasonic oscillator when the ultrasonic oscillator is housed in the ultrasonic-oscillator housing part.

5. The ultrasonic endoscope according to claim 1, wherein the first sealing member has a uniform thickness in a normal direction of a surface of the first sealing member, which is in contact with a corresponding one of the side surfaces of the ultrasonic oscillator when the ultrasonic oscillator is housed in the ultrasonic-oscillator housing part.

6. The ultrasonic endoscope according to claim 2, wherein the first sealing member has a uniform thickness in a normal direction of a surface of the first sealing member, which is in contact with a corresponding one of the side surfaces of the ultrasonic oscillator when the ultrasonic oscillator is housed in the ultrasonic-oscillator housing part.

7. The ultrasonic endoscope according to claim 3, wherein the first sealing member has a uniform thickness in a normal direction of a surface of the first sealing member, which is in contact with a corresponding one of the side surfaces of the ultrasonic oscillator when the ultrasonic oscillator is housed in the ultrasonic-oscillator housing part.

8. The ultrasonic endoscope according to claim 4, wherein the first sealing member is elastic in a thickness direction corresponding to the normal direction.

9. The ultrasonic endoscope according to claim 5, wherein the first sealing member is elastic in a thickness direction corresponding to the normal direction.

10. The ultrasonic endoscope according to claim 6, wherein the first sealing member is elastic in a thickness direction corresponding to the normal direction.

11. The ultrasonic endoscope according to claim 7, wherein the first sealing member is elastic in a thickness direction corresponding to the normal direction.

12. The ultrasonic endoscope according to claim 1, further comprising a second sealing member provided between the bottom surface of the ultrasonic oscillator and the ultrasonic-oscillator housing part.

13. The ultrasonic endoscope according to claim 1, further comprising a second sealing member provided between the bottom surface of the ultrasonic oscillator and the ultrasonic-oscillator housing part.

14. The ultrasonic endoscope according to claim 1, wherein the wiring connection unit is provided on the bottom surface of the ultrasonic oscillator.

15. The ultrasonic endoscope according to claim 12, wherein the wiring connection unit is provided in a central part of the bottom surface, and the second sealing member is provided in a peripheral part of the bottom surface.

16. The ultrasonic endoscope according to claim 13, wherein the wiring connection unit is provided in a central part of the bottom surface, and the second sealing member is provided in a peripheral part of the bottom surface.

17. The ultrasonic endoscope according to claim 14, wherein the wiring connection unit is provided in a central part of the bottom surface, and the first sealing member is provided in a peripheral part of the bottom surface.

18. The ultrasonic endoscope according to claim 1, wherein the resin is thermoplastic resin.

* * * * *